United States Patent
Tennakoon et al.

(10) Patent No.: US 6,949,178 B2
(45) Date of Patent: Sep. 27, 2005

(54) ELECTROCHEMICAL METHOD FOR PREPARING PEROXY ACIDS

(75) Inventors: Charles L. K. Tennakoon, College Station, TX (US); K. Scott McKenzie, Bryan, TX (US); Michelle Will, Bryan, TX (US); Elizabeth I. H. McGrew, Bryan, TX (US)

(73) Assignee: Lynntech, Inc., College Station, TX (US)

( * ) Notice: Subject to any disclaimer, the term of this patent is extended or adjusted under 35 U.S.C. 154(b) by 474 days.

(21) Appl. No.: 10/191,815

(22) Filed: Jul. 9, 2002

(65) Prior Publication Data

US 2004/0007476 A1 Jan. 15, 2004

(51) Int. Cl.$^7$ .............................................. C25B 1/28
(52) U.S. Cl. ....................... 205/439; 205/440; 205/455; 204/263; 204/265; 204/256
(58) Field of Search ................ 205/439, 440, 205/455; 204/263, 265, 256

(56) References Cited

U.S. PATENT DOCUMENTS

| | | | |
|---|---|---|---|
| 5,069,880 A | 12/1991 | Karlson | |
| 5,087,419 A | 2/1992 | Lutz | |
| 5,122,538 A | 6/1992 | Lokkesmoe et al. | |
| 5,266,275 A | 11/1993 | Faddis | |
| 5,290,406 A | 3/1994 | Sawamoto et al. | |
| 5,759,489 A | 6/1998 | Miura et al. | |
| 5,770,033 A | * 6/1998 | Murphy et al. | ............. 205/464 |
| 5,972,196 A | * 10/1999 | Murphy et al. | ............. 205/466 |
| 6,022,512 A | 2/2000 | Tanaka et al. | |
| 6,171,551 B1 | 1/2001 | Malchesky et al. | |
| 6,387,238 B1 | 5/2002 | Merk et al. | |
| 2004/0245116 A1 | * 12/2004 | Ohsaka et al. | ............. 205/455 |

FOREIGN PATENT DOCUMENTS

WO   WO 01/07099   2/2001

* cited by examiner

*Primary Examiner*—Arun S. Phasge
(74) *Attorney, Agent, or Firm*—Streets & Steele; Jeffrey L. Streets; Frank J. Campigotto (57) ABSTRACT

A method and apparatus for the generation and collection of an aqueous peracid solution at the cathode of a PEM electrolyzer. The electrochemical process introduces carboxylic acid (such as distilled table vinegar, lactic acid, citric acid or combinations) to the anode and a source of oxygen to the cathode. The PEM electrolyzer has a gas diffusion cathode having a cathodic electrocatalyst that is capable of hydrogen peroxide generation. The peracid solution is generated at the gas diffusion cathode and the solution is very pure and may be used for disinfecting or sterilizing various items or solutions. In a second embodiment, the carboxylic acid may be provided directly to the cathode, such as in the form of an acid vapor.

75 Claims, 5 Drawing Sheets

ELECTROCHEMICAL METHOD FOR PREPARING PEROXY ACIDS

BACKGROUND OF THE INVENTION

1. Field of the Invention

The present invention relates to an apparatus and electrochemical method for preparing peracids.

2. Description of the Related Art

Peracids have long been used as chemical reagents and bleaching agents in industrial chemical processes. Some peracids are effective biocides and so are often used as microbial and scale inhibitors in water treatment systems. Increasingly, dilute aqueous solutions of peracids are being used as disinfectants in environmental, agricultural, medical, and food processing applications. In 1986, peracetic acid received FDA approval for use as a clean-in-place ("CIP") oxidizer in the food and beverage industry. More recently, peracetic acid products have received FDA approval for direct use on fruits and vegetables A peracid is the oxidized derivative of a carboxylic acid, for example, peracetic acid ($CH_3COOOH$) is the oxidized derivative of acetic acid ($CH_3COOH$). Peracids are strong oxidizing agents and most (e.g., per acetic acid, per lactic acid, etc.) are completely soluble in water. Thus, peracid solutions provide an alternative to chlorine, ozone or hydrogen peroxide solutions, especially for applications where off-gassing is a concern. Peracids are germicidal and readily decompose into non-toxic constituents. However, peracids have been found to be sporicidal and remain effective at dilute concentrations even in the presence of organic matter. In fact, cooling tower studies show that peracetic acid remains effective at concentrations as low as 3 to 5 ppm.

Some advantages of using aqueous peracid solutions for sterilizing and disinfecting applications are attributable to the fact that peracids are: (1) sporicidal, bactericidal, virucidal and fungicidal at dilute concentrations (5–35 ppm) in water; (2) effective against non-tuberculous mycobacteria including chelonae, HIV, hepatitis B viruses, microorganisms, spores, viruses and fungi; (3) capable of denaturing proteins and enzymes; (4) soluble in lipids and so is not deactivated by microbial enzymes like catalase and peroxidases; (5) rapidly decomposed into the parent carboxylic acid, water and oxygen without leaving toxic residues; and (6) safe for use in sterilizing medical instruments and equipment, disinfecting food preparation surfaces and cleaning floors, walls, plumbing, dishes, and toys.

Antimicrobial compositions are particularly needed in the food and beverage industries to clean and sanitize processing facilities such as pipelines, tanks, mixers, etc. and continuously operating homogenization or pasteurization equipment. Other uses for antimicrobial compositions include vegetable washing and disinfection, meat surface decontamination, poultry chiller baths, processing equipment, cleaning and disinfecting beverage containers, sterilizing point-of-use and point-of-entry water purification devices, terminal sterilization and treatment of contaminated infectious waste. The biocidal activity of peracids results from its oxidation of sulfhydryl groups (—SH), disulfide bonds (S—S) and double bonds in proteins, lipids and other cellular constitutents to disrupt the chemiosmotic functions of the cell membrane. This broad oxidizing capability controls biofilm and scale deposits by eliminating the accumulation of biomass, mold, mildew, algae, fungi and bacteria on numerous surfaces and in aqueous systems in general.

The presence of disease causing microorganisms, disinfection byproducts and other toxic substances in drinking water poses a great health risk to humans. Point of use activated carbon filters and reverse osmosis ("RO") units are becoming increasing popular with consumers for water purification. These water purification devices are primarily used for removing municipal disinfectants, i.e., chlorine, and metals from tap water. However, if bactericides are not used, the filtration media and membranes quickly become a breeding ground for heterotrophic (HTPC) bacteria.

Because some peracids have a high oxidation potential, these same peracids are excellent biocides even at dilute concentrations. In contrast, hydrogen peroxide needs 100 times greater concentrations to achieve comparable biocidal activity. However, at these higher concentrations, the off-gassing of hydrogen peroxide can become a limiting factor. Furthermore, hydrogen peroxide does not retain its antimicrobial activity in the presence of interfering compounds, because it reacts indiscriminately with dissolved oxidizable substances such that the amount of hydrogen peroxide available for disinfection is drastically reduced. However, when used in solution with peracids, lower concentrations of hydrogen peroxide can be used. In fact, mixtures of hydrogen peroxide and peracids can enhance the disinfecting and sterilizing of a variety of materials including surgical and medical devices.

In most applications, it is preferable to use dilute aqueous solutions of peracids (ppm level) for sterilizing or disinfecting. However, because peracids are so highly reactive, it is relatively costly to synthesize, transport and deliver peracids as oxidizing agents using conventional processes. For example, a 1% solution of peracetic acid loses half its strength through hydrolysis in six days. In this regard, peracetic acid is less stable than hydrogen peroxide and becomes increasingly less stable when diluted. For this reason, stabilizers are often added to undiluted peracid solutions which must then be diluted prior to use. Clearly a more efficient process for generating peracids at the "point of use" would greatly increase their use by the general public.

Peracids are typically produced by chemical synthesis as a result of mixing carboxylic acid and hydrogen peroxide with an inorganic acid catalyst in a reaction vessel. For example, peracetic acid is commercially produced by the reaction of hydrogen peroxide with acetic acid (or acetic anhydride) using concentrated sulfuric acid as a catalyst. Because the peracids generated are highly reactive, stabilizers are added to maintain the oxidizing capacity of peracids during storage and shipment. Furthermore, because many of these additives and other process by-products are toxic or hazardous, they entail more costly storage, handling and transportation costs. These additives are retained in the peracid product and generally require further treatment prior to use or disposal. Clearly a process capable of generating high purity solutions of peracids would be beneficial.

Peracids can also be produced in electrochemical cells wherein the desired reactions are carried out by imposing an electric current across electrodes immersed in an electrically-conducting fluid, such as water. In an electrochemical cell, the liquid acid catalyst is replaced by, solid electrolyte, such as a perfluoronated sulfonic acid polymer, thus eliminating the need for corrosive acids.

U.S. Pat. No. 5,122,538 (Lokkesmoe et al.) discloses a process for generating peracid in a packed-bed type reaction vessel charged with a cation-exchange resin (e.g., sulfonic acid resin). The resin catalyzes the reaction between the hydrogen peroxide and a carboxylic acid to produce peracids. One problem with this method is that the hydrogen peroxide causes the resins to swell. To reduce this swelling, the catalyst bed must be regenerated with chelating agents prior to introducing the reaction mixture. Common chelating agents include ethylene-diaminetetraacetic acid (EDTA), nitrilotriacetic acid (NTA) and organic phosphates, such as phytic acid. The resins may degrade in the presence of oxidizing agents which can introduce contaminants into the peracid product and limit catalyst life in general. In addition, some of the chelating agents and reaction products present in the resulting product are toxic. Thus, health and safety concerns limit or prevent the direct application of peracids generated by this process for medical sterilization, food processing and consumer product applications.

U.S. Pat. No. 6,171,551 B1 (Malchesky et al.) discloses a method for generating peracid at the anode of an electrochemical cell. The process generates the oxidizing species, e.g., a mixture of ozone and hydrogen peroxide in the anode compartment. These oxidizing species are then reacted with an aqueous organic acid solution within the anode to produce a peracid solution in the anode compartment. After sufficient concentrations of the peracid are formed, the anode product containing peracid and the oxidizing species are withdrawn from the anode compartment. In addition, it is disclosed that a lag-time of between one and two hours is needed before any detectable levels of the oxidizing species are produced. This means that the method is not conducive to continuous operation, and highly inappropriate for use as a POU/POE device. Furthermore, the reported bench-scale results indicate that the quantities of hydrogen peroxide and peracetic acid produced are very low.

Existing electrochemical peracid generating processes suffer from many disadvantages including low production rates and the potential for introducing toxic constituents. In addition, in the preparation of peracids by the chemical synthetic route, the use of concentrated hydrogen peroxide (30–70%) as a raw material and also the use of concentrated sulfuric acid as a catalyst pose safety problems for transportation, storage and handling of the reactants and the catalyst. In fact, because peroxide solutions are unstable, inorganic stabilizers are generally added to prevent off-gassing of hydrogen peroxide. Further, additional stabilizers are used to stabilize peracids. Amongst those which have found wide application include dipiconilic acid, for example as disclosed in U.S. Pat. No. 2,609,391. Other compounds include phosphonates, notably those disclosed in British patent No. 925,373. In other instances, a combination of stabilizers are employed, for example the combinations of dipicolinic acid and phosphonates disclosed in International application publication Nos. WO91/07375 and WO91/13058. The use of stabilizers and other additives can introduce further toxic or otherwise hazardous compounds into the peracid solution.

Therefore, there exists a need for an apparatus and a method that can generate high purity peracid solutions without any toxic or otherwise undesirable by-products and thereby, promote their use in numerous disinfecting and sterilizing applications. There is also a need for a method and apparatus that produces peracids quickly and essentially on demand. It would be desirable if the method and apparatus would provide POU/POE generation of peracids.

SUMMARY OF THE INVENTION

The present invention provides a method for the electrochemical synthesis of peracids in an electrochemical cell having an ionically conducting membrane in intimate contact between an anode and a gas diffusion cathode. The method comprises supplying an aqueous organic acid solution to the anode, supplying a source of oxygen to the cathode, and generating peracid at the cathode. Water from the aqueous organic acid solution supplied to the anode is oxidized to produce protons. The method further comprises transporting the aqueous organic acid solution through the ionically conducting membrane to the gas diffusion cathode and withdrawing the peracid from the cathode.

The oxygen supplied to the cathode is reduced in the gas diffusion cathode to produce hydrogen peroxide and the peracid.

The present invention further provides an apparatus for generating a peracid comprising an electrochemical cell having an ion conducting membrane in intimate contact between an anode and a cathodic catalyst layer of a gas diffusion cathode, an aqueous organic acid solution in communication with the anode, and a source of oxygen in communication with the gas diffusion cathode. Optionally, the organic acid may be delivered directly to the cathode as organic acid vapor instead of, or in combination with, delivering the organic acid in water to the anode. The electrochemical cell is preferably operated at a current density greater than one Ampere per square centimeter or even at a current density greater than 0.2 Ampere per square centimeter.

The gas diffusion cathode includes a gas diffusion layer and a cathodic catalyst layer, wherein the cathodic catalyst layer contacts the ion conducting membrane, such as a proton conducting membrane. The gas diffusion layer includes hydrophobic pathways and hydrophilic pathways therethrough. The gas diffusion layer preferably comprises carbon cloth or carbon paper fiber impregnated with a sintered mass derived from fine carbon powder and a polytetrafluoroethylene emulsion, wherein the carbon powder provides the hydrophilic pathways and the polytetrafluoroethylene provides the hydrophobic pathways. Preferably, the gas diffusion layer comprises carbon cloth or carbon paper fiber impregnated with carbon or graphite with or without an additional catalyst, such as pyrolyzed cobalt porphyrin catalyst.

The cathodic catalyst layer comprises a proton exchange polymer, polytetrafluoroethylene polymer and a metal selected from cobalt, nickel, platinum, palladium, gold, iridium or mixtures thereof. The cathodic catalyst layer preferably comprises carbon or graphite with or without an additional catalyst, such as pyrolyzed cobalt porphyrin. More preferably, the cathodic catalyst layer comprises a proton exchange polymer, polytetrafluoroethylene polymer and a carbon-supported pyrolyzed cobalt-porphyrin. Preferably, the gas diffusion layer comprises carbon cloth or carbon paper fiber impregnated with a carbon-supported pyrolyzed cobalt porphyrin catalyst.

The anode comprises a substrate selected from porous titanium, titanium suboxides, platinum, tungsten, tantalum, hafnium and niobium. The anode comprises an anodic catalyst selected from ruthenium dioxide, platinum-tungsten alloys or mixtures, glassy carbon, platinum, and combinations thereof. The ionically conducting membrane is a proton exchange membrane, which may comprise a perfluoronated sulfonic acid polymer. The ionically conducting membrane is bonded to the gas diffusion cathode.

In an alternative embodiment, the present invention provides a method for electrochemical synthesis of peracids in an electrochemical cell having an ionically conducting membrane in intimate contact between an anode and a gas diffusion cathode, the method comprising supplying an organic acid and a source of oxygen to the cathode, supplying water to the anode, and generating peracid at the cathode. The method further comprises transporting the organic acid as a vapor with the oxygen source to the gas diffusion cathode and withdrawing the peracid from the cathode. Water is oxidized at the anode to generate protons and oxygen is reduced in the gas diffusion cathode to produce hydrogen peroxide and the peracid.

BRIEF DESCRIPTION OF THE DRAWINGS

So that the above recited features and advantages of the present invention can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

The apparatus of the invention comprises one or more electrochemical cells where each cell has an anode and a cathode separated by an ionically conducting membrane. In the preferred apparatus, the anode and cathode compartments are separated by a proton exchange membrane ("PEM"), having a first side in contact with the anode and a second side bonded to the catalyst layer of a gas diffusion cathode. Peracids are produced electrochemically at the cathode by (1) directly or indirectly supplying an organic acid to the cathode; (2) providing for proton flow across the PEM; and (3) supplying a source of oxygen gas to the gas diffusion cathode, wherein the gas diffusion cathode includes a gas diffusion layer and a catalyst layer. The peracid product may then be removed from the cathode chamber of the system, preferably as an aqueous peracid solution. Electric current is passed through the anode and the gas diffusion cathode, which are separated by the PEM. Protonated organic acids or other peracid precursors that are provided to the anode, or formed at the anode, pass through the PEM reacting with oxygen (or peroxides) in the cathodic catalyst layer to generate the peracid product through oxygen reduction.

The organic acid may be indirectly supplied to the cathode by providing an aqueous organic acid solution to the anode. The term "aqueous", as that term is used herein in reference to solutions, means that the solutions contain at least some water, but is not limited to solutions where water comprises a majority of the solution. Alternatively, the organic acid may be directly supplied to the cathode by providing an organic acid vapor to the gas diffusion cathode, such as along with the required oxygen by bubbling oxygen gas through an acid solution, such as vinegar or glacial acetic acid. It should be recognized that the invention may operate with the organic acid being supplied indirectly to the cathode through the anode, directly to the cathode, or a combination of these two routes. Other and further modes of delivering organic acid to the cathode may also be employed, either alone or in combination with these methods.

Typically, the PEM separating the anode and cathode is kept moist by supplying water to the anode. This moisture is necessary to hydrate the sulfonate sites on the polymer to allow for proton transfer through the membrane. Alternatively, the membrane may be kept moist by humidifying the oxygen source to the cathode. Optionally, water can be introduced directly to the PEM by installing tubing within the PEM that delivers moisture via capillary action. It should be recognized that the invention may operate with the moisture being provided in any one or more of the foregoing modes. Other and further modes of delivering moisture to the PEM may also be employed, either alone or in combination with these methods.

In order to drive the electrochemical reaction, it is necessary to apply electric power to the cell electrodes. The electrochemical reactions are progressed by electric potential differences imposed by applying an electrical current (preferably DC) between the anode and the cathode. The electrodes are connected through electrical leads to an external source of electric power with the polarity being selected to induce anion flow towards the anode and the cation flow towards the cathode. Optionally, the electrodes may be retractable as described in U.S. patent application Ser. No. 09/598,067 and the U.S. patent application filed on Dec. 10, 2001, Express Mail No. EL833794883US, entitled "Electrochemical Apparatus with Retractable Electrode", both of which are incorporated by reference herein.

The present invention also encompasses the use of a multi-cell arrangement, otherwise referred to as a stack or "plate-and-frame" arrangement. This arrangement stacks individual cells back to back, in series so that the electrical current flows from one cell to the next adjacent cell. Each cell is separated by an electrically conducting bipolar plate that allows the electricity from the anode of one cell to pass through to the cathode of an adjacent cell. The cathode of each cell must also be provided with organic acids and a source of oxygen gas.

Preferably, the anode comprises a substrate and a catalyst coating wherein the substrate is selected from the group consisting of porous titanium, titanium suboxides, platinum, tungsten, tantalum, hafnium, and niobium. The anodic catalyst coating can be selected from the group consisting of ruthenium dioxide, iridium oxide, platinum, platinum-tungsten alloys, or mixtures thereof. Accordingly, the one or more catalyst layers are deposited on the substrate (porous frit), the PEM, or both the PEM and porous frit. The oxide catalyst powder mix is bonded to the PEM using a Nafion solution followed by heat treatment. The catalyst layer is bonded to the metal frits by either spraying or by painting a solution or a slurry consisting of a mixture of required metal chlorides (such as iridium chloride or ruthenium chloride) and by subsequent heat treatment to form the required oxide mixture (such as iridium oxide or ruthenium oxide).

Preferably, the PEM is made of a polymer material having sulfonate functional groups contained on a fluorinated carbon backbone. Two such materials include: NAFION® (manufactured by DuPont) having an equivalent weight of 1100 grams; and an experimental PEM (XUS-13204.20) manufactured by the Dow Chemical Company of Midland, Mich. ("Dow") having an equivalent weight of 800 grams. While NAFION® 105, 115 and 117 will each operate satisfactorily in the present invention, NAFION® 117 is the preferred NAFION® product. Even more preferably, the PEM is reinforced for dimensional stability, such as those reinforced membranes described in U.S. Pat. Nos. 5,547,551 and 6,042,958, which patents are incorporated by reference herein.

The gas diffusion cathode comprises a gas diffusion layer of carbon cloth or carbon paper fiber that is impregnated with a sintered mass derived from carbon powder, a perfluoronated sulfonic acid polymer, and polytetrafluoroethylene (PTFE) emulsion. Preferably, the gas diffusion cathode comprises a polytetraflurorethylene-bonded, semi-hydrophobic catalyst layer supported on a hydrophobic gas diffusion layer. Accordingly, the one or more catalyst layers are deposited on the gas diffusion layer, the PEM, or both the PEM and gas diffusion layer. Preferably, the cathodic electrocatalyst is a macrocyclic transition metal complex in which the metal is selected from the group consisting of platinum, cobalt, nickel, palladium, gold, iridium, iron or mixtures thereof. A particularly preferred cathodic catalyst is cobalt tetrakis (4-methoxyphenyl) porphyrin. Usually, this catalyst is first deposited on graphitized or nongraphitized carbon powder before bonding onto the gas diffusion electrode or the PEM using either a PTFE emulsion or a Nafion solution. However, for certain applications it may be desirable to use carbon, graphite or other forms of carbon as the only catalyst.

The present invention provides an electrochemical method for generating peracids at the cathode. An electric current is imposed across electrodes disposed on opposing sides of a sheet of a proton-conducting material, preferably a proton-exchange membrane (PEM). Reagents consisting of a source of oxygen (e.g. air) and a simple organic acid solution, such as distilled table vinegar (typically 2–10% acetic acid), are suitable. The oxygen is provided directly to the cathode and the organic acid is preferably provided as an aqueous organic acid solution delivered indirectly to the cathode by electroosmotic transport through the PEM from the anode compartment.

In a preferred embodiment, the organic acid, such as carboxylic acid, is continuously introduced into the anode compartment and a source of oxygen is continuously introduced into the cathode compartment. When an electric current is imposed between the electrodes, water present at the anode dissociates into oxygen ($\frac{1}{2}O_2$) and protons ($2H^+$). The protons liberated at the anode are transferred across the proton-exchange membrane separating the anode and cathode compartments. In addition, the protons liberated in the anode compartment protonate the organic acids, or other peracid precursors, such that these compounds have a net positive charge and are transferred across a proton-exchange membrane ("PEM") by electroosmosis. Additionally, the organic acids present in the anode compartment may diffuse to the cathode compartment across the PEM because of the high concentration in the anode compartment and a negligible concentration in the cathode compartment.

The protonated organic acids delivered to the cathode contact one or more cathodic electrocatalysts and oxygen from the incoming source of oxygen. The source of oxygen to the cathode compartment may be pure oxygen, air, oxygen-enriched air, a mixed gas stream containing oxygen, or an oxygen-containing gas stream generated in the anode compartment. The peracid product generated may be periodically or continually removed from the cathode compartment through a product delivery port.

Where the organic acid is to be supplied directly to the cathode, the anode only needs to be supplied with water (preferably distilled water), while the oxygen-containing stream entering the cathode compartment can be fed with an organic acid vapor, such as a carboxylic acid vapor. This can be easily achieved by bubbling oxygen gas or air through an organic acid solution before being provided to the cathode compartment. In this embodiment of the invention, the protons generated in the anode compartment and transferred to the cathode electrocatalyst across the PEM provide the acidic environment on the catalyst surface to bring about the desired reaction.

The invention generates peracids at the cathode, thereby eliminating the need for supplies of hydrogen peroxide solutions and corrosive mineral acids. The present electrochemical method of producing peracids also provides certain advantages over chemical methods, including eliminating much of the corrosive nature of the peracid due to the absence of sulfuric acid (especially when generated at the point-of-use), eliminating the need for adding inorganic stabilizers, and eliminating the health and safety issues relating to unstable peroxides, corrosive mineral acids and toxic residues.

The process of the invention provides a high purity peracid product that is especially well suited for use in numerous disinfecting or sterilizing applications. The peracid product can be delivered and used directly from the generator without requiring further purification, separation, or addition of stabilizers, although additional processing steps are not prohibited. If needed or desired for a specific application, the peracid product can be diluted with water to provide a lesser concentration of peracid. Since the peracid product may be produced as it is needed, there is no longer a great concern that the dilute peracid will degrade prior to use. The peracid product can be used immediately after being produced in a variety of applications including, but not limited to, direct injection into a water stream, a filtration device, a system for sterilizing medical instruments and equipment, food handling and processing equipment, or direct use onto pathogen-contaminated surfaces (e.g., processing fresh produce or uncooked meats).

In accordance with the invention, the peracid generator may be integrated with systems that require sterilization, optionally to provide an automated system for periodic sterilization. Optionally, the electrochemical peracid generator can be integrated with numerous other water treatment modules, including reverse osmosis, tubular membrane separators, sterile filters, activated carbon filters or the like. Optionally, the method may include the further step of diluting the peracid product with water (or other solvent) until the solution reaches the desired concentration for the service of interest.

In any event, peracids can be generated on demand using one or more embodiments of the invention without any hazardous handling, transportation, storage or disposal concerns. The concentration and delivery rate of the peracid product can be customized by varying the applied current, electrode materials, cell size, total active area, and catalyst configuration. Because the starting solutions and their by-product constitutents are non-toxic and biodegradable, the invention is safe for use in a wide variety of consumer and commercial disinfecting applications.

The term "sanitizing", as used herein, means a reduction in the population of microorganisms by about 5 powers (i.e., at least 5 orders of magnitude). The composition may also be used to achieve disinfection or sterilization (i.e., elimination of all microorganisms) by employing higher levels of active biocides (peracids) in the use solutions. Disinfection and sterilization are truly lethal in their effects. It is to be emphasized that at the lower peracid concentrations, the instant peracid solution provides sanitizing performance. At still lower peracid concentrations, the peracid solution provides a "biostatic" capability where the organisms, in the presence of the solution are inhibited from growing, but upon removal from the agent, the organisms can again multiply.

The process of the present invention generates peracid solutions from simple organic acids (e.g., distilled table vinegar available at grocery stores) and oxygen. Because the surrounding air can provide an acceptable supply of oxygen, the only commodities that must be provided in the preferred process are electricity and organic acids, both of which are readily obtainable. The anti-microbial peracid solutions generated are effective in both killing and preventing growth of unwanted microorganisms.

Notably, these peracid solutions can inactivate bacterial spores within protein films. In addition, the peracid solutions can be diluted with water to low concentrations and yet still maintain their effectiveness.

While any simple organic acids (peracid precursors) may be supplied in accordance with the present invention, the organic acids are preferably carboxylic acids. The peracid formed from carboxylic acid, for example, is the oxidized derivative of those carboxylic acids. Because the hydrogen atom of the carboxy group is active and the carboxy group may appear as an anion, carboxylic acids have a tendency to acidify aqueous solutions in which they are present. Carboxylic acids have the formula R—COOH, where the "R" may represent any number of different groups including aliphatic groups, alicyclic groups, aromatic groups, heterocycic groups, or mixtures thereof. These "R" groups may be saturated or unsaturated as well as substituted or unsubstituted. Specifically, the inventors have found that peracetic acid and perlactic acid concentrations greater than 5 ppm, such as in the 5–35 ppm range, are capable of eliminating a range of microorganisms including spores and viruses on numerous surfaces.

The electrochemical systems of the present invention clearly lend themselves to "point-of-use" ("POU") and "point of entry" ("POE") applications. The "point of entry" is generally accepted to be the place where water or other material to be disinfected enters the home or facility. For example, a POE water treatment device processes water for the entire home or facility. In contrast, a "point of use" application typically refers to the general location at which water or other material is used. For example, a POU/POE water treatment device processes and dispenses water directly for washing, cleaning, disinfecting or the like. For the purpose of the present invention, "point of use" may also mean a counter-top unit for producing a high purity aqueous peracid solution as needed for disinfecting food, utensils or other home articles. In this respect, the invention overcomes the problems associated with stocking, re-supply and dispensing of acceptable and controlled levels of peracid disinfectants in general.

The ability to continuously generate dilute peracid solutions having a high oxidating potential in combination with a low environmental impact make this invention particularly well suited for various POU/POE consumer applications, such as washing and disinfecting foods (such as fruits, vegetables and meats), countertops, sinks, bathroom surfaces, cookware, utensils, toys, medical items and the like. Peracid solutions can also be used for cleaning medical instruments or for transport or processing of food products. Peracid solutions may be used as a general purpose disinfecting solution for use in applications including but not limited to: medical instruments and products, dental products, cooling towers, sewage treatment, treatment of medical wastes, animal carcass rinsing and elimination of pathogens from numerous hard surfaces. The consumption of peracids is low because they can be diluted into an aqueous stream, yet retain their effectiveness as oxidizing agents. Furthermore, peracids remain effective in the presence of organic loading on the surfaces to be cleaned.

The peracid generator of the present invention can even be integrated into various POU/POE devices to provide either pre-treatment or post-treatment disinfection. Any residual level of the peracid biocide (or the parent organic acid) can be easily removed by a carbon filter or rejected by the reverse osmosis unit. Peracids may also be used to prevent the biofouling of other POU/POE devices used for water filtration. The peracid generator can also be easily retrofitted into small community water systems rural municipal water districts and for water purification at or near the point at which water is consumed, such as refrigerators, water fountains, soda dispensers, hospital wards and restaurants.

Figure 1:
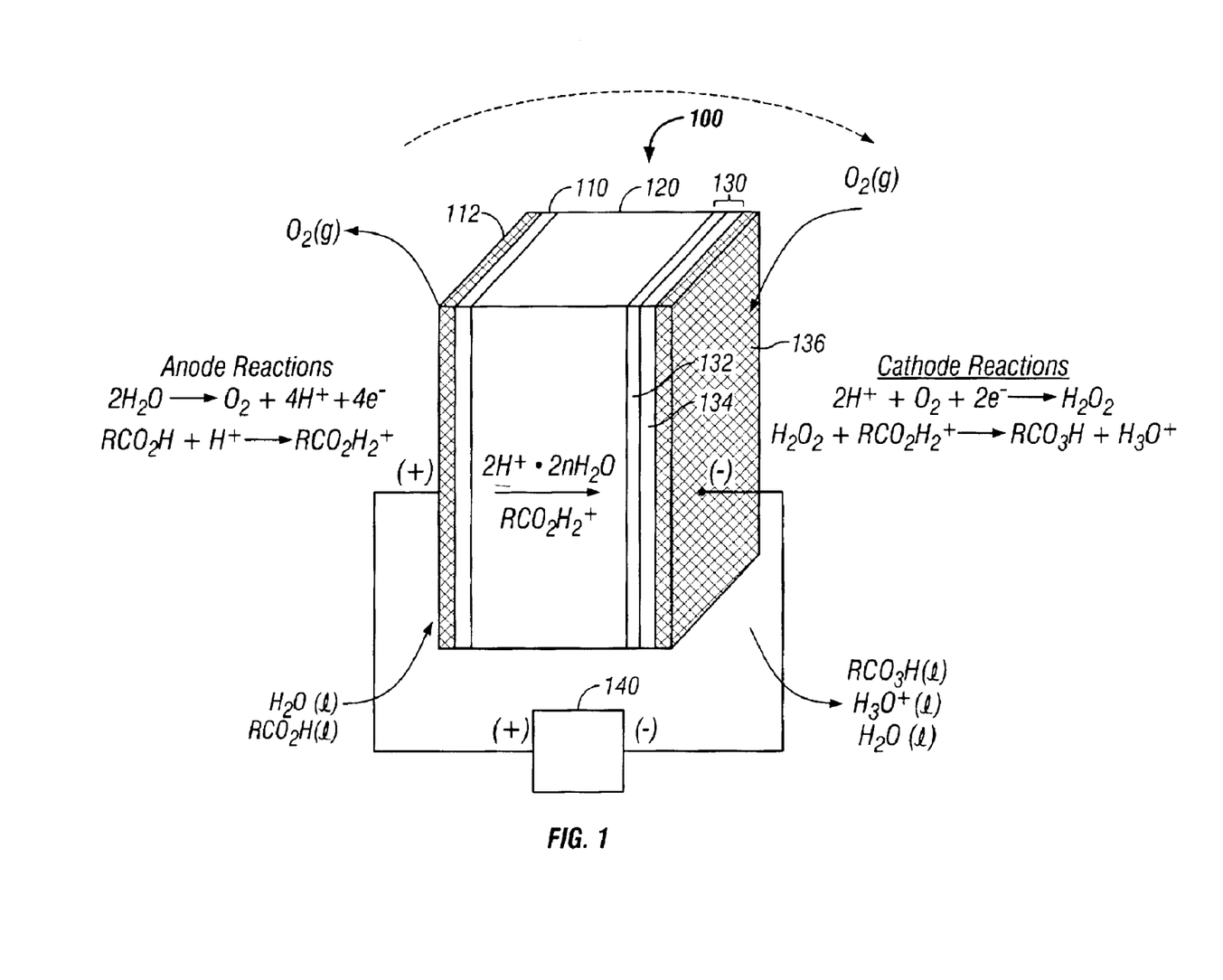
FIG. 1 is a schematic diagram of an electrochemical cell showing the oxidation and reduction reactions believed to be involved in the present method of producing peracids at the cathode utilizing a carboxylic acid introduced to the anodic compartment.

FIG. 1 is a schematic diagram of an electrochemical cell 100 showing the oxidation and reduction of ionic species capable of producing one or more peracids at the cathode 130. As illustrated, the electrochemical cell 100 consists of at least one positively-charged electrode, the anode 110, in contact with a current collector/flowfield 112 that is externally connected to the positive pole of an external power supply 140; and at least one negatively-charged electrode, the cathode 130, in contact with a current collector/flowfield 136 that is externally connected to the negative pole of the power supply 140. Preferably, the cathode 130 consists of a gas diffusion layer 134, such as ELAT (manufactured by E-Tek), on which an electrocatalyst layer 132 is deposited.

An electrolyte 120 separates the anode 110 from the cathode 130 and controls the flow of dissolved ionic species between them. As illustrated, a dilute aqueous solution of organic acid (carboxylic acid) is fed to the anode 110 where oxygen gas liberated and the organic acid is protonated. It is believed that the preferred electrochemical reactions taking place at the anode are:

$$2H_2O \rightarrow O_2 + 4H^+ + 4e^- \qquad \text{EQUATION (1)}$$

H$^+$ions generated according to equation (1) protonate the carboxylic acid according to the following reaction.

$$RCOOH + H^+ \rightleftharpoons RCOOH_2^+ \qquad \text{EQUATION (2)}$$

Generally, the organic acid is protonated, however it should be noted that other peracid precursors may also be present. These cations, the protonated organic acid and protons, are transferred through the PEM 120 towards the negatively-charged cathode 130 along with a small amount of water. Generally, each cation is hydrated with 3–5 molecules of water depending upon the charge and size of the cations. The function of the PEM 120 is to promote the transfer of hydrogen ions, protonated organic acids and certain other positively-charged precursors and prevent the mixing of anode and cathode fluids. Some unprotonated organic acid is also transported across the PEM to the cathode by diffusion from a higher concentration in the anode compartment to a lower concentration in the cathode compartment.

Generally speaking, the protons and protonated acids are conducted from the anode 110 to the cathode 130 through the PEM 120 and the electrons are conducted from the anode 110 to the cathode 130 via the external circuit 140. The protons and electrons are then recombined at the cathode 130 in the presence of oxygen to form hydrogen peroxide and peracid.

The compartment containing the cathode 130 is fed with oxygen, such as in air, to enable the production of hydrogen peroxide at the cathode 130 by the reduction of the oxygen. The hydrogen peroxide then reacts with the protonated acids and other peracid precursors to form peracid product on the catalyst surface 132. Optionally, oxygen evolved at the anode 110 can be collected and separately routed to the cathode 130. The cathodic reactions involving the reduction of oxygen are:

$$O_2 + 2H^+ + 2e^- \rightarrow H_2O_2 \qquad \text{EQUATION (3)}$$

$$O_2 + 4H^+ + 4e^- \rightarrow 2H_2O \qquad \text{EQUATION (4)}$$

EQUATION (3) shows the reduction of oxygen to form hydrogen peroxide. Note that EQUATION (4) represents the generation of water, however for clarity the reduction of oxygen to water at the cathode 130 is not shown in FIG. 1. Utilization of low over-potentials and certain electrocatalysts selectively enhance hydrogen peroxide formation reaction and suppress the water formation reaction. In addition, a small amount of water will be transported across the PEM 120 to the cathode 130, because each cation is hydrated with 3–5 molecules of water depending on the charge and size of the cation. Peracid can be formed at the cathode 130 by rapid electrophilic attack of the hydrogen peroxide on the protonated organic acid or other peracid precursors according to the following reactions:

$$RCOOH_2^+ + H_2O_2 \Leftrightarrow RCOOOH + H_2O + H^+ \qquad \text{EQUATION (5)}$$

$$RCOOH + H_2O_2 \Leftrightarrow RCOOOH + H_2O \qquad \text{EQUATION (6)}$$

The peracid reaction is an equilibrium reaction that may be driven to the right (favoring peracid production) by the removal of hydrogen ions or by the use of excess reagents. In relation to EQUATION (5), when R="CH$_3$" the peracid generated is peracetic acid, and when R="CHOHCH$_3$" the peracid generated is perlactic acid.

Depending on the specific cathodic electrocatalyst configuration 132, other oxidizing and reducing species may be present at the cathode that may cause the equilibrium concentrations to shift. While the peracid product can be generated at the cathode 130 in the absence of peroxides, hydrogen peroxide can also be produced at the cathode 130 in combination with peracid to produce a mixed disinfectant product. Furthermore, the peracid product can be generated at the cathode 130 in the presence of other organic and inorganic compounds and numerous oxidizing and/or reducing agents. Alternatively, peracids can be generated at both the anode 110 and the cathode 130, by providing peracid precursors to the anode 110 in the presence of ozone, where the ozone is generated electrolytically in the anode.

Figure 2:
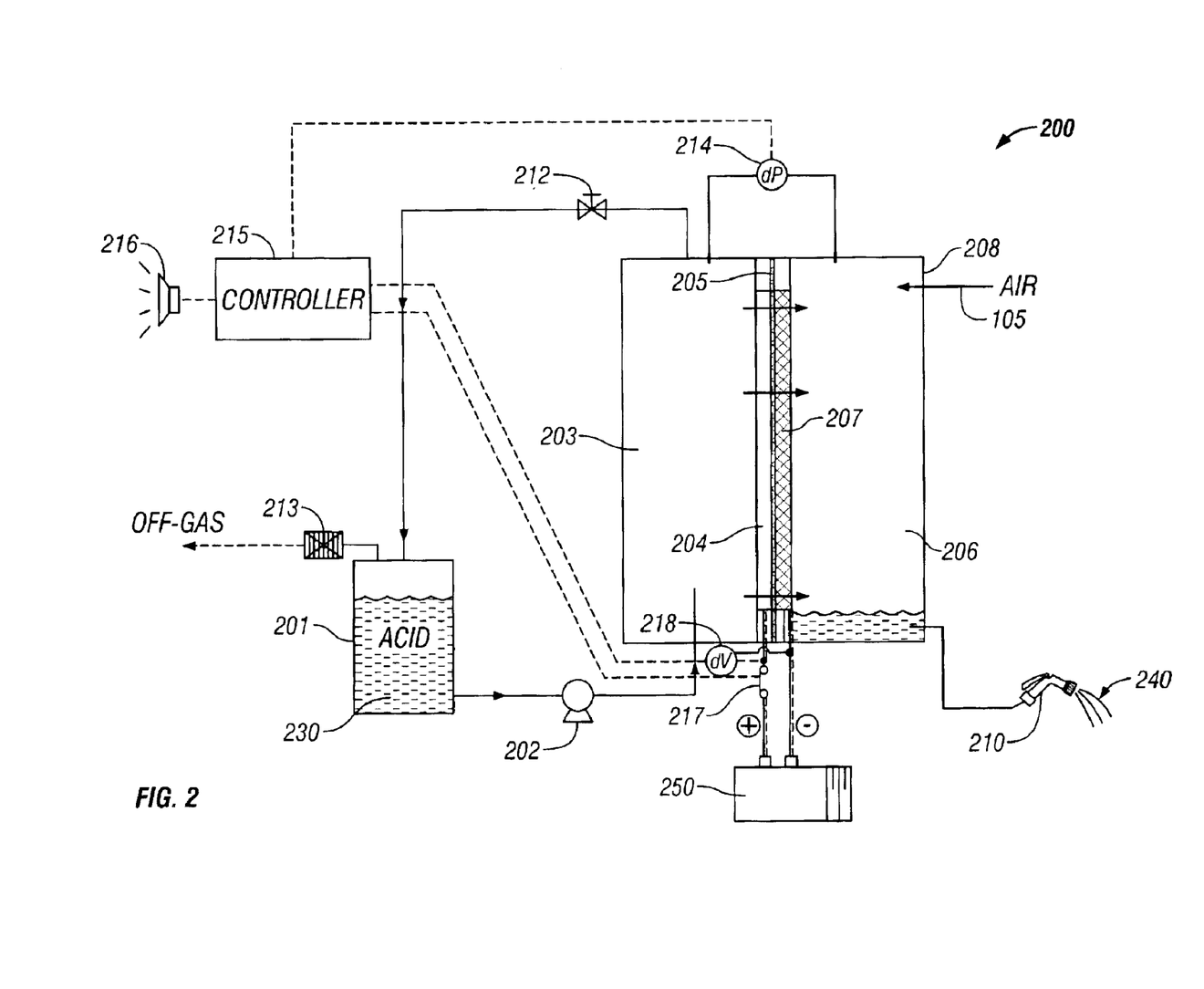
FIG. 2 is a block flow diagram of an electrochemical system, having an electrochemical cell as shown in FIG. 1, used for producing peracids in a cathode compartment, showing the flow path of the various reagents and product streams passing through the system.

FIG. 2 shows an electrochemical peracid generator 200, associating piping and instruments capable of producing a disinfectant solution, specifically a peracetic acid solution 240, from table vinegar 230. As illustrated, the components of the peracid generator 200 include a reservoir 201 containing the organic acid (i.e., vinegar) 230 to be converted, a circulation pump 202, an anode compartment 203 containing an anode 204, and a cathode compartment 206 containing a cathode 207, separated by a cation exchange membrane 205. Preferably, the generator 200 uses a DC power source 250, such as an AC/DC converter or a battery. This arrangement allows the generator 200 to be used as a point-of-use cleaning and disinfecting device capable of meeting a variety of consumer needs.

The present electrochemical method for generation of a disinfecting aqueous solution of peracids 240 requires the use of electrocatalysts on both the anode 204 and the cathode 207. The catalyst used on the anode 204 surface plays an active role in generating the protonated organic acid and other peracid precursors. As illustrated, the cell 200 generates peracetic acid product 240 from table vinegar 230. However, it should be noted that the cell 200 will generate perlactic acid when lactic acid is used as the source carboxylic acid in reservoir 201. Furthermore, it should be recognized that various carboxylic acids, including mixtures of carboxylic acids, may be used to produce corresponding peracids.

In the preferred method, the electrochemical cell has a gas diffusion electrode as the cathode 207 and a platinized porous titanium anode 204. The anode compartment is fed with a dilute aqueous solution of organic acid, i.e., distilled table vinegar (typically 4–10% acetic acid solution) 230. The organic acid is protonated at the anode 204, with oxygen gas being liberated.

Preferably, air 105 provides the primary source of oxygen for the cell. Air 105 may be introduced through port 208 into the cathode compartment 206. Hydrogen peroxide generated electrolytically at the cathode 207 via oxygen reduction, then reacts with the protonated organic acid or other peracid precursors at the cathode 207 to form peracid product 240. Alternative sources of oxygen include oxygen-enriched air and pure oxygen, such as the oxygen generated in the anode compartment 204.

Preferably, the hydrophobic membrane 205 is a proton exchange membrane (PEM), such as NAFION® 117 (manufactured by DuPont), in contact with a catalyst surface on an anodic substrate such as porous titanium, and also in contact with a catalyst on the surface of a gas diffusion electrode constructed of a porous substrate material such as ELAT (manufactured by E-Tek). The purpose of the PEM 205 is to transfer protons from the anode 204 to the cathode 207 and further to prevent the solution in the anode compartment 203 from mixing with the peracid product 240 in the cathode compartment 206.

In the preferred method, the electrochemical peracid generator 200 may be operated under pressure sufficient to deliver peracid product 240 from the cathode compartment 206 without the need for a delivery pump. However, a delivery pump can be provided upstream of the delivery nozzle 210, if desired. Optionally, the anode compartment 203 and cathode compartment 206 may be maintained at different pressures and the system equipped with a differential pressure sensor 214 or other means of monitoring the pressure differential across the hydrophobic membrane 205. The measured pressure differential 214 can be provided to a controller 215 for comparison with a predetermined reference or range as a means to detect failure of membrane 205 or loss of integrity of cell 200. Should the pressure differential fall outside the preferred range, a visual or audible indicator 216 can be provided to alert the user of system problems. Optionally, the system may include a switch 217, enabling the controller to shut down all power to the cell when the pressure differential falls outside the preferred range.

Suitable inlet and outlet passages are also provided in the cell headspace to permit the withdrawal of off-gas from the anode compartment 203 and the cathode compartment 206. The two gas removal systems are typically maintained separate in order to isolate the cathode gases from the anode gases. A headspace valve 212 located on the anode compartment 203 off-gas line and the air intake blower 208 located on the cathode compartment 206 allow the electrochemical cell 200 to be pressurized for delivery of peracid product 240 through a delivery nozzle 210 or other point-of-use delivery attachment.

Off-gas generated in the anode compartment 203 may be routed to a gas handling unit 213 in order to remove any gases that may effervesce from solution. Alternatively, if a flow-through air or oxygen cathode is employed, any oxygen gas generated in the anode compartment 203 can be routed to the cathode 207. This transfer can be accomplished by operating the anode compartment 203 at pressure higher than the cathode compartment 206.

A variety of embodiments known to those skilled in the art, are possible for selectively transferring ionic species to the cathode compartment 206. In fact, the ionic species transferred depends on the specific type and concentration of carboxylic acids 230 used and the type and materials of the electrolyte 205 and catalysts used. For example, it may be desirable to dilute certain precursors (e.g. acetic acid or perlactic acid) to lesser concentrations prior to introducing the precursors to the anode compartment 203.

In accordance with one application for using the peracid product 240 that has been generated at the cathode 207 of the peracid generator, the peracid can be introduced into one or more upstream water treatment modules such as reverse osmosis (RO), activated carbon, ultrafiltration or tubular membrane system, to prevent the growth and accumulation of biofilms which are known to reduce the functionality of such treatment units. These water treatment modules can be provided independent of the peracid generator for example, a purification device installed directly on the kitchen faucet line. Peracid solution 240 can be periodically diverted from the cathode compartment 206 to flush and disinfect the water treatment module. Optionally, tap water can be used to dilute the peracid product 240 prior to delivery or use.

Optionally, a visual or audible indicator may be used to provide an indication to the user as to the performance of the electrochemical peracid generator 200. In one embodiment, the indication is the result of measuring the voltage across, and/or the current through, the electrochemical cell 200. The output of the electrochemical cell may be correlated to the operating parameters of the cell 200 and may therein be used to monitor system performance. As an example, the voltage between the anode 204 and cathode 207 of the electrochemical cell 200, as measured by voltage meter 218, may be used to determine if the cell 200 is properly producing peracid product 240.

Figure 3:
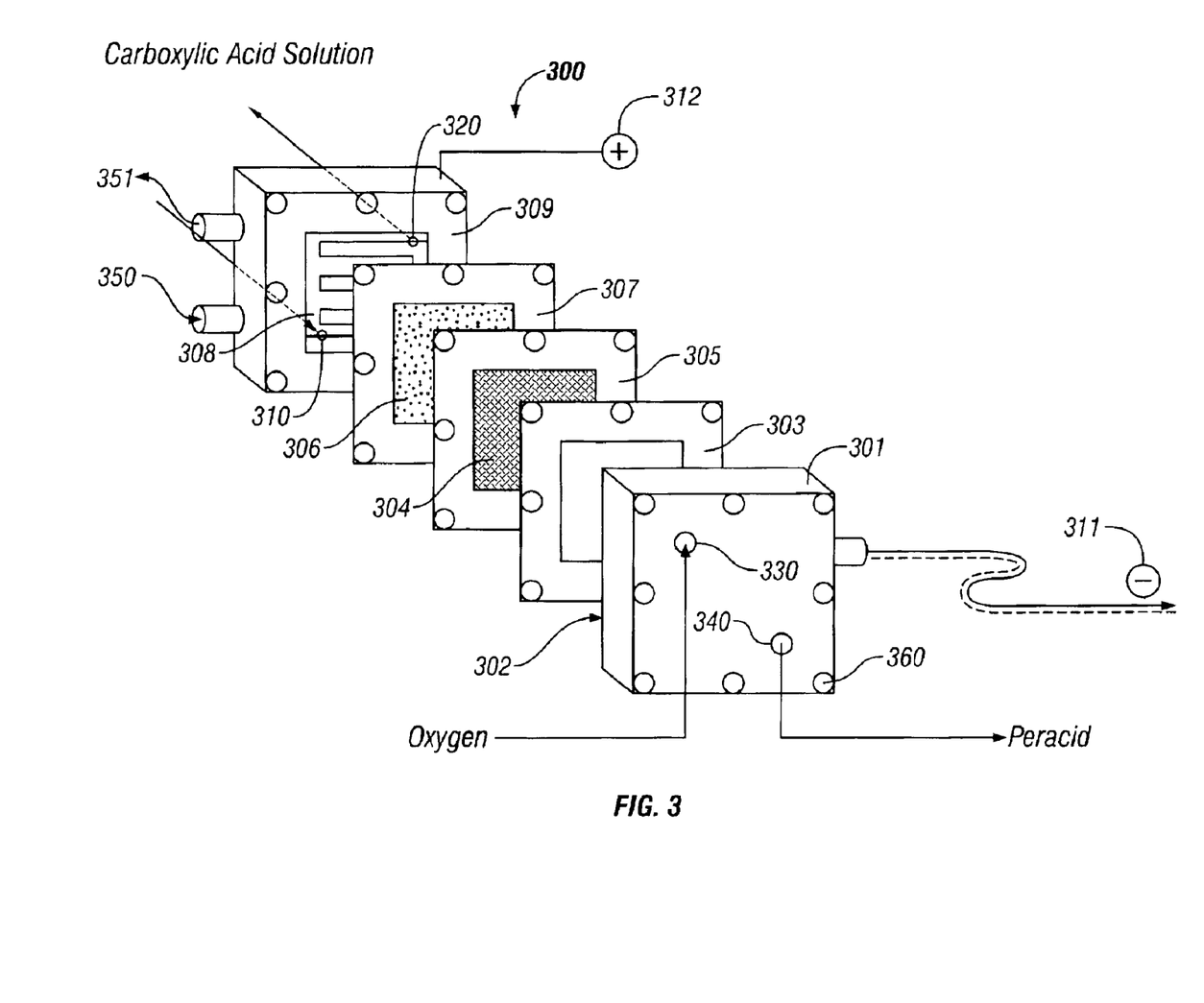
FIG. 3 is a cross-sectional diagram of a plate-and-frame embodiment of a single electrochemical cell that shows a preferred catalyst configuration capable of generating peracids continuously at the cathode.

FIG. 3 is an exploded cross-sectional view of an electrochemical cell stack 300 comprised of a series of components used for generating peracids at the cathode. This embodiment allows the electrochemical peracid generator to operate in a nearly or entirely passive manner with simplicity of design. Each electrochemical cell 300 includes a proton exchange membrane (PEM) 305 in contact with a gas diffusion cathode 304 having a cathode catalyst and in contact with a porous anode substrate 306 having an anode catalyst. The cathode and anode substrates are backed by flow fields 302 and 308, respectively, that optionally serve as a means of support for the porous materials serving as the anode and the cathode.

The electrochemical cell stack 300 may include any number of individual cells, but is shown here with a single electrochemical cell having a titanium end plate 301 having an expanded titanium flowfield 302 (cathode side), a PTFE gasket 303, a gas diffusion cathode 304 having the cathodic catalyst formulation deposited on the surface facing the PEM 305, the PEM 305, a porous titanium frit 306 having a anodic catalyst deposited on the surface facing the PEM 305, a second PTFE gasket 307, a titanium flowfield (anode side) 308, and a titanium end plate 309. The titanium end plate 301 and the porous titanium frit 306 are provided with electrically-conducting leads 311 and 312 respectively, to provide electrical connections to the electrodes. It should be recognized that the flowfields 301, 309 may be machined in the endplates or comprise standalone elements. Other variations of the cell will be apparent to those skilled in the art.

As illustrated, the proton exchange membrane (PEM) or solid polymer electrolyte 305, preferably, a sheet of perfluorinated sulfonic acid polymer constructed of NAFION® 117 (manufactured by DuPont), is disposed in the center of the cell. Bonded to one side of the PEM (the cathode side) is the electronically conducting, semi-hydrophobic, oxygen-reduction electrocatalyst layer of the gas diffusion cathode 304. This electrocatalyst layer of the cathode 304 may be comprised of a catalyst and a binder. The cathodic electrocatalyst may be carbon, graphite, other forms of carbon, macrocyclic transition metal complex or combinations thereof. The binder may be PTFE, PFSA or combinations thereof. The electrocatalyst may then be bonded to the gas diffusion electrode surface using a Nafion solution instead of a Teflon suspension. Preferably, the gas diffusion layer of the cathode 304 is integrally formed onto the catalyst layer dispersed in a Nafion solution and then coated on the PEM 305.

Optionally, the PEM 305 can be placed in contact with a carbon fiber paper that has the cathodic catalyst formulation deposited thereon.

On the other side (the anode side) of the PEM 305 is the anode 306 made up of a catalyst layer formed on a substrate. The electronically conducting, hydrophilic anodic electrocatalyst layer is preferable made of ruthenium dioxide ($RuO_2$) or a RuIrOx or a platinum-tungsten alloy. The anode substrate is a porous, non-corroding, electronically conducting support material that is preferably fabricated using sintered titanium (or tantalum) particles.

Two non-conducting PTFE gaskets 303 and 307 are placed on either side of the PEM 305 to function as a seal so that the anode and cathode can operate as isolated systems. The gaskets 303, 307 have cutouts to fit around the perimeter of the cathodic gas diffusion cathode 304 and the anode substrate 306, respectively. These cutouts provide internal manifolding that allows fluid to flow to and from the electrode/electrolyte interfaces. Preferably, the gasket should have a thickness greater than that of the gas diffusion cathode 304 and the anode substrate 306 so that it may be sufficiently compressed to seal liquids and/or gases.

The elastic nature of the gaskets 303, 307 compensate for any contraction or expansion encountered in the electrochemical cell under various operating conditions. Alternatively, the gas diffusion electrode 304 and titanium frit coated with the anode electrocatalyst 306 are inserted into an injection molded frame to provide an absolutely flush and flat surface against the PEM 305.

The source carboxylic acid solution (e.g., vinegar) enters the cell 300 through port 310, enters flowfield 308 and contacts the anode catalyst layer 306 where oxygen, protonated organic acid and other peracid precursors are produced. The anolyte solution is preferably collected in the opposing manifold and withdrawn from the cell stack 300 through port 320 and optionally returned to the source carboxylic acid reservoir (not shown) for recirculation. In a similar manner, oxygen gas (or oxygen in air) enters the cell 300 through port 330 in fluid communication with flowfield 302, flows through the center cutout region of PTFE gasket 303, and contacts the gas diffusion cathode 304. Oxygen functions as a cathodic depolarizer to generate the peracid product which is withdrawn from the cell stack 300 through port 340. Preferably, the cell 300 is configured to prevent gas traps and thus ensure that any off-gas exits the cell with the circulating carboxylic solution through port 320. Preferably, the cell 300 is cooled by circulating water (i.e., tap water) through tubing extending along the flowfields. The cooling water enters the endplate 309 through port 350 and exits the end plate through port 351. Optionally, the circulating carboxylic acid may be sufficiently cooled in the source reservoir (not shown) to dissipate the net thermal energy released from the reactions.

Each cell component has a plurality of bolt holes 360 around its perimeter edge for aligning and securing the components in place. To keep the end plates 301, 309 electrically isolated from each other, a plurality of electrically insulating sheaths and washers can be used in conjunction with the bolts used to compress the cell (not shown). Having electrically isolated end plates 301 and 309, a negative terminal (or busbar) 311 and a positive terminal (or busbar) 312 can be connected to a DC power source.

Alternatively, an apparatus for the electrolytic generation of peracid may comprise a plurality of individual electrolytic cells 300 which are similar in construction and operation. This multi-cell "plate-and frame" arrangement can accommodate numerous cells in series operation by inserting additional cell modules between the end plates 301 and 309. Each cell has an anode 306, a PEM 305 and a gas diffusion/catalyst cathode 304, as described above. This mult-cell arrangement preferably has further sections removed for internal manifolding to allow fluid to flow to and from the electrode/electrolyte interfaces. Clamping means are used to secure the end plates and electrolytic cells tightly together as described above.

Figure 4:
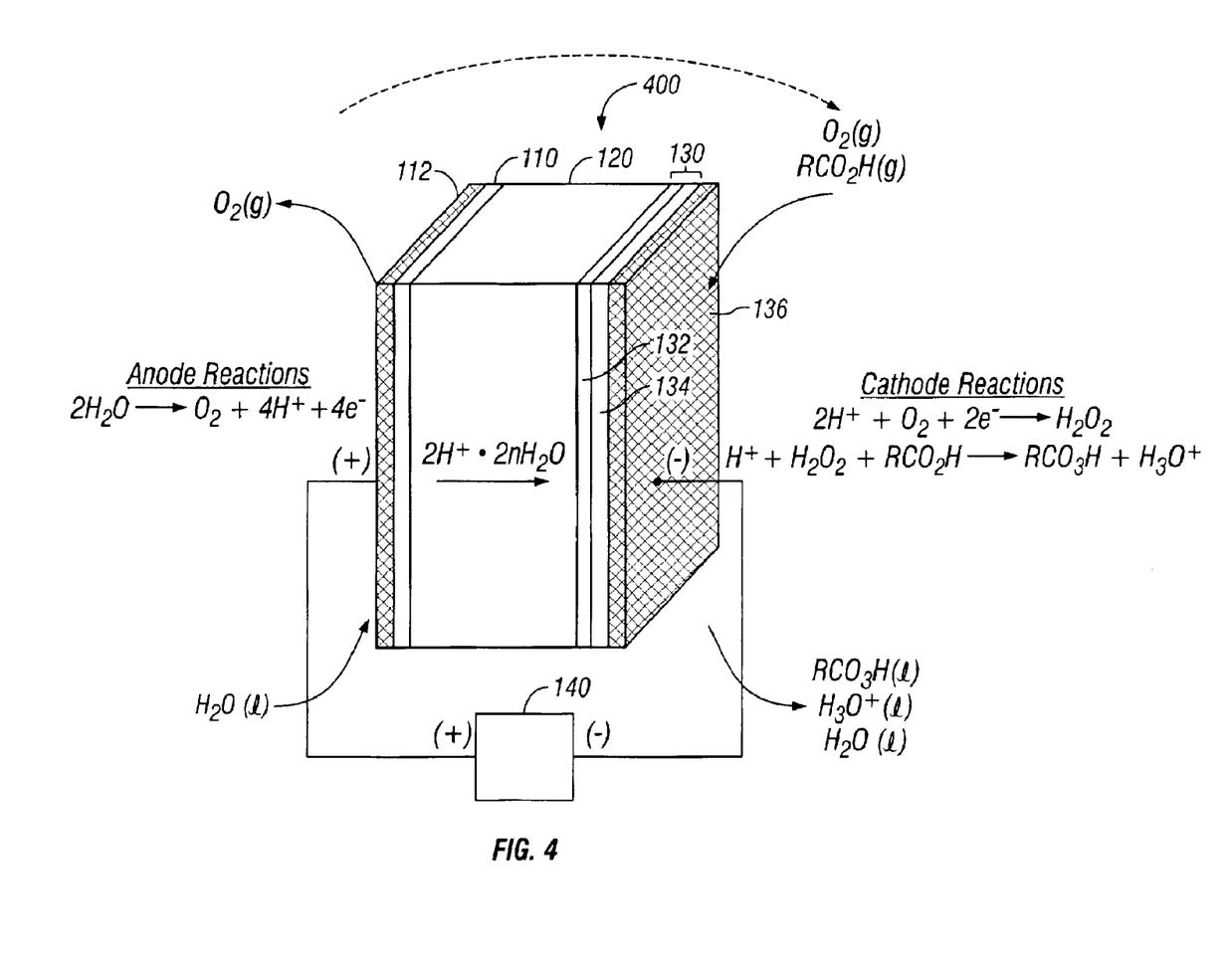
FIG. 4 is a schematic diagram of an electrochemical cell showing the oxidation and reduction reactions believed to be involved in the present method of producing peracids at the cathode with a carboxylic acid introduced to the cathodic compartment.

FIG. 4 is a schematic diagram of an electrochemical cell 400 showing the oxidation and reduction of ionic species capable of producing one or more peracids at the cathode 130, with the required carboxylic acid introduced to the cathode compartment as an acid vapor with the oxygen from the oxygen source. As illustrated, the electrochemical cell 400 consists of at least one positively-charged electrode, the anode 110, that is externally connected to the positive pole of an external power supply 140; and at least one negatively-charged electrode, the cathode 130, which is externally connected to the negative pole of the power supply 140. Preferably, the cathode 130 consists of a gas diffusion layer 134, such as ELAT (manufactured by E-Tek), on which an electrocatalyst layer 132 is deposited.

A polymer electrolyte membrane (PEM) 120 separates the anode 110 from the cathode 130 and controls the flow of dissolved ionic species between them. As illustrated, water is fed to the anode 110 where oxygen gas is liberated and $H^+$ ions and electrons are generated as previously shown in equation (1). The $H^+$ ions are transferred through the PEM 120 towards the negatively charged cathode 130 along with a small amount of water. Generally, each cation is hydrated with 3–5 molecules of water depending upon the charge and size of the cations. The function of the PEM 120 is to promote the transfer of hydrogen ions, but the PEM also provides an electronically non-conducting separator between the anode and cathode fluids.

The $H^+$ ions are conducted from the anode 110 to the cathode 130 through the PEM 120 and the electrons are conducted from the anode 110 to the cathode 130 via the external circuit 140. The protons and electrons are then recombined at the cathode 130 in the presence of oxygen to form hydrogen peroxide which is a reactant used to making the peracid.

The cathode 130 compartment is supplied with oxygen, such as in air, to generate hydrogen peroxide at the cathode 130 by the reduction of oxygen (as shown in equations (3) and (4) above). The cathode is also provided with carboxylic acid vapor. The carboxylic acid is first protonated, as shown before in equation (2), with the $H^+$ ions generated on the anode side. The hydrogen peroxide then reacts with the protonated acids and other peracid precursors to form peracid product on the catalyst surface 132. Optionally, oxygen evolved at the anode 110 can be routed to the cathode 130.

Utilization of low over potentials and certain electrocatalysts selectively enhance hydrogen peroxide formation reaction and suppress the water formation reaction of equation (4). In addition, a small amount of water will be transported across the PEM 120 to the cathode 130, because each cation is hydrated with 3–5 molecules of water depending on the charge and size of the cation. Peracid can be formed at the cathode 130 by a rapid electrophilic attack of the hydrogen peroxide on the protonated organic acid or other peracid precursors according to the reactions shown in equations (5) and (6) above.

Figure 5:
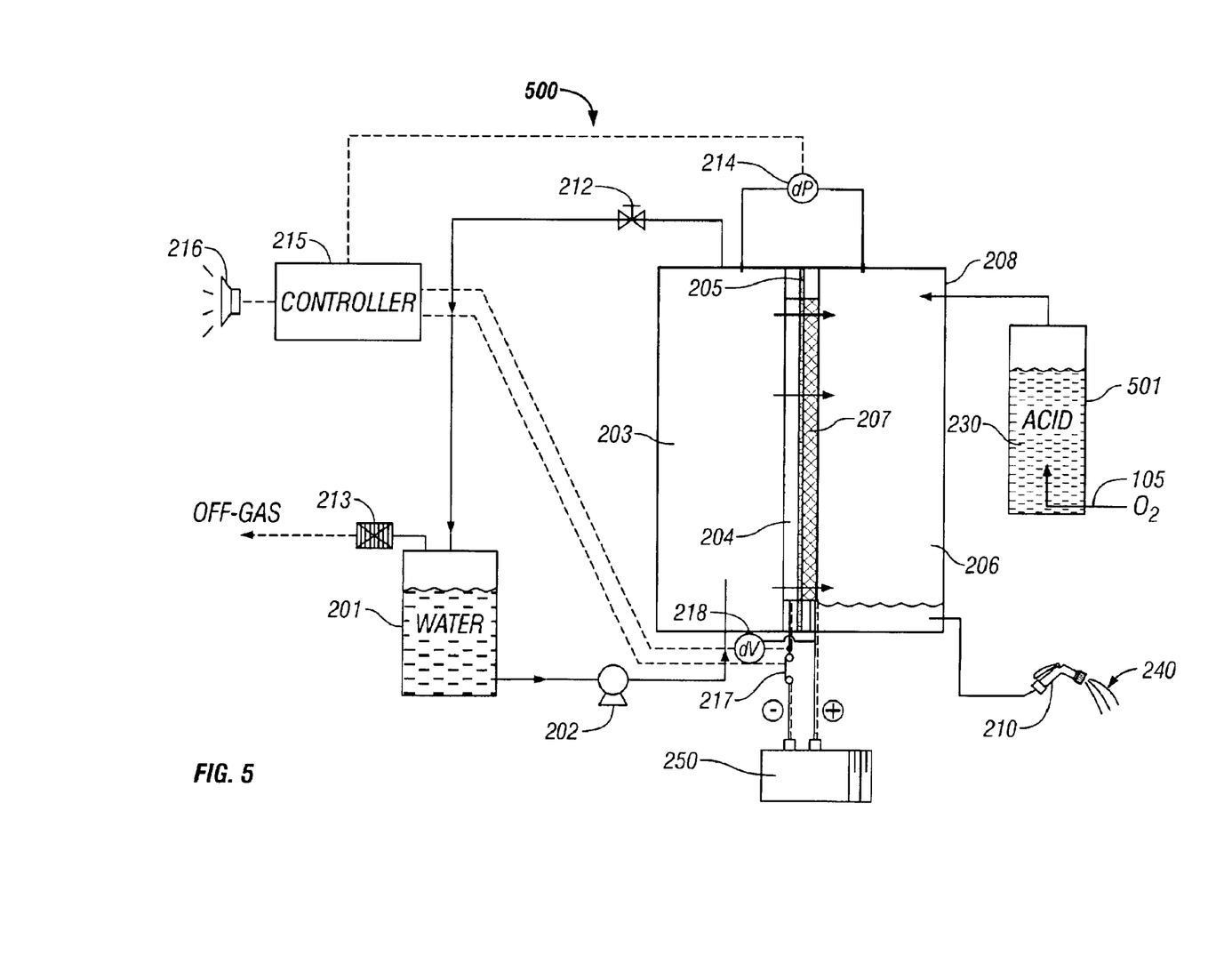
FIG. 5 is a block flow diagram of an electrochemical system, having an electrochemical cell as shown in FIG. 4, used for producing peracids in a cathode compartment, showing the flow path of the various reagents and product streams passing through the system.

FIG. 5 shows an electrochemical peracid generator 500, associating piping and instruments capable of producing a disinfectant, specifically peracetic acid 240, from table vinegar 230. Except as discussed below, the electrochemical peracid generator 500 is constructed and operated in the same manner as the generator 200 of FIG. 2 and the associated discussion.

In the embodiment of FIG. 5, the oxygen source or air 105 is bubbled through the acid in the acid reservoir 501 so that the oxygen carries acid vapors into the cathode compartment 206. Oxygen 105 and acid 230 may be introduced through port 208 into the cathode compartment 206. Hydrogen peroxide is generated electrolytically at the cathode 207 via oxygen reduction, which then reacts with the protonated organic acid or other peracid precursors at the cathode 207 to form peracid product 240. Alternative sources of oxygen include oxygen-enriched air and pure oxygen, such as the oxygen generated in the anode compartment 204 and released as off-gas from the gas handling unit 213.

EXAMPLE 1

A peracid generator was designed and fabricated using components installed in a "plate-and-frame" type arrangement in accordance with FIG. 3. A single electrochemical cell having dimensions of 3 in.×3 in.×1 in. was assembled with seven components: (1) a titanium end plate; (2) a PTFE gasket (anode side); (3) a porous titanium plate coated with anodic catalyst; (4) a solid electrolyte (proton exchange membrane); (5) a gas diffusion electrode coated with a cathodic catalyst formulation; (6) a PTFE gasket (cathode side); and (7) a titanium end plate.

The proton exchange membrane was constructed from a 5 inch×5 inch sheet of NAFION® 117 (manufactured by DuPont).

The anode substrate was a 0.065 inch thick porous titanium frit (Astromet Ti-ASTM B265) having a pore size of 25–40 microns. Ruthenium dioxide and iridium dioxide mixture ($RuIrO_x$) deposited on the titanium frit provided an effective surface area of approximately 25 $cm^2$.

The cathode consisted of a carbon cloth gas diffusion electrode (ELAT/NC/SS/V2 supplied by E-Tek). The cathodic catalyst was formulated as an ink consisting of 25 mg of 5 wt % cobalt tetrakis (4-methoxyohenoil) porphyrin (CoTMPP) deposited on carbon (Vulcan-XCR72R, Cabot). A further 25 mg of uncoated Vulcan was mixed with 0.85 g of 5 w/v % NAFIO® solution (DuPont). And then, 1 drop 1% solution of surfactant (Ethoquad C/25; Akzo Noble Chemicals Inc; McCook, Ill.) was added to the catalyst paint mixture that was used to paint the ELAT gas diffusion carbon cloth. This mixture was sonicated for three hours and then painted on the ELAT gas diffusion carbon cloth. The painted ELAT was cured at 100° C. for 10 minutes and then at 125° C. for a further 10 minutes in an air-draft furnace. The area on which the catalyst was deposited was approximately 25 $cm^2$.

The anode compartment was fed with a vinegar solution (4% acidity) purchased from a local grocery store. This solution was delivered from an anodic reservoir to provide a single flow pass through the cell. A voltage ranging from 2.0 to 2.6 volts was applied across the cell. Pure oxygen was continually supplied to the cathode compartment. The peracid product was withdrawn from the cathode compartment and analyzed for peracid content using the ABTS spectrophotometric method capable of determining peracid content in the presence of hydrogen peroxide. The biocidal activity of the peracid product for disinfecting biofilms, pathogenic bacteria and viruses was confirmed. Approximately 15.6 mL/hr of peracetic acid was produced. The operating conditions and the results of these two runs are set out in Table 1.

TABLE 1

| Ex. | Catalyst | Current (A) | Voltage (V) | Output (mL/h) | Organic acid precursor | Peracid conc. (wt %) |
|---|---|---|---|---|---|---|
| 1 | (25 mg Vulcan + 25 mg CoTMPP on Vulcan) + surfactant | 10 | 2.8 | 15.0 | vinegar (5%) | 3.1% peracetic |
| 2 | (20 mg Vulcan + 5 mg CoTMPP on Vulcan) + surfactant | 10 | 2.6 | 13.7 | vinegar (5%) | 2.7% peracetic |
| 3 | (25 mg Vulcan + 5 mg CoTMPP on Vulcan) + surfactant | 10 | 2.3 | 16.0 | vinegar (5%) | 3.3% peracetic |
| 4 | (40 mg Vulcan + 10 mg CoTMPP on Vulcan) + surfactant | 10 | 2.7 | 16.3 | vinegar (5%) | 4.6% peracetic |
| 5 | (40 mg Vulcan + 10 mg CoTMPP on Vulcan) + surfactant | 10 | 2.7 | 15.0 | lactic acid (5%) | ~5.0% perlactic |

EXAMPLE 2

A peracid generator was designed and fabricated substantially in accordance with the configuration and materials described in Example 1. The only difference from the peracid generator of Example 1 was that the cathodic catalyst ink did not contain any cobalt tetrakis (4-methoxyohenoil) porphyrin (CoTMPP). Rather, carbon served as the only catalyst in the ink. Otherwise, the ink was prepared, applied, and cured in the same manner as in Example 1.

The types of carbon materials used may have difference surface densities. For example, an ungraphitized carbon (Vulcan-XCR72R, Cabot) was found to have a surface area of 210 square meters/gram. After graphitizing, this same carbon was found to have a surface area density of 86 square meters/gram. By contrast, a carbon powder was obtained by crushing carbon beads (Carbon Pearls 2000, Cabot), wherein the carbon powder has a surface area density of 1475 square meters/gram.

In two separate runs, the anode compartment was fed first with an aqueous solution of 9% citric acid and then with an aqueous solution of 9% acetic acid or vinegar. Pure oxygen was continually supplied to the cathode compartment. The peracid product was withdrawn from the cathode compartment and analyzed for peracid content using the ABTS spectrophotometric method capable of determining peracid content in the presence of hydrogen peroxide. The operating conditions and the results of these two runs are set out in Table 2.

TABLE 2

| Catalyst | Current | Voltage | Output | Organic acid precursor | Peroxyacid concentration |
|---|---|---|---|---|---|
| Carbon Pearl 2000 (25 mg) surfactant, Nafion solution (binder) | 10 A | 2.5 V | 15 mL/hour | 9% Citric acid | 1925 ppm |
| Carbon Pearl 2000 (25 mg) surfactant, Nafion solution (binder) | 10 A | 2.7 V | 14 mL/hour | 9% Vinegar (acetic acid) | 114 ppm |

It will be understood from the foregoing description that various modifications and changes may be made in the preferred embodiment of the present invention without departing from its true spirit. It is intended that this description is for purposes of illustration only and should not be construed in a limiting sense. The scope of this invention shall be limited only by the language of the following claims.

What is claimed is:

1. A method for electrochemical synthesis of a peracid in an electrochemical cell having an ionically conducting membrane in intimate contact between an anode and a gas diffusion cathode, the method comprising:

supplying an aqueous organic acid solution to the anode;

supplying a source of oxygen to the cathode;

imposing an electrical potential between the anode and cathode; and forming the peracid at the cathode.

2. The method of claim 1, further comprising:

transporting the aqueous organic acid solution through the ionically conducting membrane to the gas diffusion cathode.

3. The method of claim 1, further comprising:

withdrawing the peracid from the cathode.

4. The method of claim 1, further comprising:
reducing the oxygen in the gas diffusion cathode to produce hydrogen peroxide and the peracid.

5. The method of claim 4, further comprising:
oxidizing water from the aqueous organic acid solution at the anode to produce protons.

6. The method of claim 1, wherein the gas diffusion cathode includes a gas diffusion layer and a cathodic catalyst layer, wherein the cathodic catalyst layer contacts the ionically conducting membrane.

7. The method of claim 6, wherein the gas diffusion layer includes hydrophobic pathways and hydrophilic pathways therethrough.

8. The method of claim 7, wherein the gas diffusion layer is comprised of carbon cloth or carbon paper fiber impregnated with a sintered mass derived from fine carbon powder and a polytetrafluoroethylene emulsion, and wherein the carbon powder provides the hydrophilic pathways and the polytetrafluoroethylene provides the hydrophobic pathways.

9. The method of claim 6, wherein the cathodic catalyst layer comprises a cation exchange polymer, polytetrafluoroethylene polymer and a metal selected from cobalt, nickel, platinum, palladium, gold, iridium or mixtures thereof.

10. The method of claim 6, wherein the cathodic catalyst layer comprises carbon-supported pyrolyzed cobalt porphyrin.

11. The method of claim 6, wherein the cathodic catalyst layer consists essentially of at least one binder and a form of carbon.

12. The method of claim 11, wherein the at least one binder is selected from polytetrafluoroethylene, a perfluoronated sulfonic acid polymer, and combinations thereof.

13. The method of claim 11, wherein the form of carbon is selected from carbon and graphite.

14. The method of claim 11, wherein the form of carbon has a surface area greater than 80 square meters per gram.

15. The method of claim 6, wherein the gas diffusion layer comprises carbon cloth or carbon paper fiber impregnated with a carbon-supported pyrolyzed cobalt porphyrin catalyst.

16. The method of claim 1, wherein the cathodic catalyst layer comprises a cation exchange polymer, polytetrafluoroethylene polymer and a carbon-supported pyrolyzed cobalt-porphyrin.

17. The method of claim 1, wherein the anode comprises a substrate selected from porous titanium, titanium suboxides, platinum, tungsten, tantalum, hafnium and niobium.

18. The method of claim 1, wherein the anode comprises an anodic catalyst selected from ruthenium dioxide, platinum-tungsten alloys or mixtures, glassy carbon, platinum, and combinations thereof.

19. The method of claim 18, wherein the anodic catalyst evolves oxygen that is substantially free of ozone.

20. The method of claim 1, wherein the ionically conducting membrane is a cation exchange membrane.

21. The method of claim 20, wherein the cation exchange membrane comprises a perfluoronated sulfonic acid polymer.

22. The method of claim 1, wherein the ionically conducting membrane is bonded to the gas diffusion cathode.

23. The method of claim 1, further comprising:
operating the electrochemical cell at a current density greater than 1 Ampere per square centimeter.

24. The method of claim 1, further comprising:
operating the electrochemical cell at a current density greater than 0.2 Ampere per square centimeter.

25. An apparatus comprising:
an electrochemical cell having a cation conducting membrane in intimate contact between an anode and a cathodic catalyst layer of a gas diffusion cathode,
an aqueous organic acid solution in communication with the anode; and
a source of oxygen in communication with the gas diffusion cathode, wherein the organic acid is transformed to a peracid at the cathode.

26. The apparatus of claim 25, wherein the gas diffusion cathode comprises a gas diffusion layer having hydrophobic pathways and hydrophilic pathways therethrough.

27. The apparatus of claim 26, wherein the gas diffusion layer is comprised of carbon cloth or carbon paper fiber impregnated with a sintered mass derived from fine carbon powder and a polytetrafluoroethylene emulsion.

28. The apparatus of claim 26, wherein the cathodic catalyst layer comprises a cation exchange polymer, polytetrafluoroethylene polymer and a metal selected from cobalt, nickel, platinum, palladium, gold, iridium or mixtures thereof.

29. The apparatus of claim 26, wherein the gas diffusion cathode comprises a gas diffusion layer including carbon cloth or carbon paper fiber impregnated with a carbon-supported pyrolyzed cobalt porphyrin catalyst.

30. The apparatus of claim 25, wherein the cathodic catalyst layer consists essentially of at least one binder and a form of carbon.

31. The apparatus of claim 30, wherein the at least one binder is selected from polytetrafluoroethylene, a perfluoronated sulfonic acid polymer, and combinations thereof.

32. The apparatus of claim 30, wherein the form of carbon is selected from carbon and graphite.

33. The apparatus of claim 30, wherein the form of carbon has a surface area greater than 80 square meters per gram.

34. The apparatus of claim 30, wherein the form of carbon has a surface area greater than 200 square meters per gram.

35. The apparatus of claim 30, wherein the form of carbon has a surface area greater than 1000 square meters per gram.

36. The apparatus of claim 25, wherein the cathodic catalyst layer comprises carbon-supported pyrolyzed cobalt porphyrin.

37. The apparatus of claim 25, wherein the cathodic catalyst layer comprises a cation exchange polymer, polytetrafluoroethylene polymer and a carbon-supported pyrolyzed cobalt-porphyrin.

38. The apparatus of claim 25, wherein the anode comprises a substrate selected from porous titanium, titanium suboxides, platinum, tungsten, tantalum, hafnium and niobium.

39. The apparatus of claim 25, wherein the anode comprises an anodic catalyst selected from ruthenium dioxide, platinum-tungsten alloys or mixtures, glassy carbon, platinum, and combinations thereof.

40. The apparatus of claim 25, wherein the cation conducting membrane comprises a perfluoronated sulfonic acid polymer.

41. The apparatus of claim 25, wherein the cathodic catalyst layer is bonded to the cation conducting membrane.

42. A method for electrochemical synthesis of a peracid in an electrochemical cell having an ionically conducting membrane in intimate contact between an anode and a gas diffusion cathode, the method comprising:
supplying an organic acid vapor and a source of oxygen gas to the cathode;
supplying water to the anode;

imposing an electrical potential between the anode and cathode; and forming the peracid at the cathode.

43. The method of claim 42, further comprising:

transporting the organic acid as a vapor with the oxygen source to the gas diffusion cathode.

44. The method of claim 42, further comprising:

withdrawing the peracid from the cathode.

45. The method of claim 42, further comprising:

reducing the oxygen in the gas diffusion cathode to produce hydrogen peroxide and the peracid.

46. The method of claim 45, further comprising:

oxidizing the water at the anode to produce protons.

47. The method of claim 42, wherein the gas diffusion cathode includes a gas diffusion layer and a cathodic catalyst layer, wherein the cathodic catalyst layer contacts the ionically conducting membrane.

48. The method of claim 47, wherein the gas diffusion layer includes hydrophobic pathways and hydrophilic pathways therethrough.

49. The method of claim 48, wherein the gas diffusion layer is comprised of carbon cloth or carbon paper fiber impregnated with a sintered mass derived from fine carbon powder and a polytetrafluoroethylene emulsion, and wherein the carbon powder provides the hydrophilic pathways and the polytetrafluoroethylene provides the hydrophobic pathways.

50. The method of claim 47, wherein the cathodic catalyst layer comprises a cation exchange polymer, polytetrafluoroethylene polymer and a metal selected from cobalt, nickel, platinum, palladium, gold, iridium or mixtures thereof.

51. The method of claim 47, wherein the cathodic catalyst layer comprises carbon-supported pyrolyzed cobalt porphyrin.

52. The method of claim 47, wherein the gas diffusion layer comprises carbon cloth or carbon paper fiber impregnated with a carbon-supported pyrolyzed cobalt porphyrin catalyst.

53. The method of claim 52, wherein the cathodic catalyst layer comprises a cation exchange polymer, polytetrafluoroethylene polymer and a carbon-supported pyrolyzed cobalt-porphyrin.

54. The method of claim 52, wherein the anode comprises a substrate selected from porous titanium, titanium suboxides, platinum, tungsten, tantalum, hafnium and niobium.

55. The method of claim 52, wherein the anode comprises an anodic catalyst selected from ruthenium dioxide, platinum-tungsten alloys or mixtures, glassy carbon, platinum, and combinations thereof.

56. The method of claim 42, wherein the ionically conducting membrane is a cation exchange membrane.

57. The method of claim 56, wherein the cation exchange membrane comprises a perfluoronated sulfonic acid polymer.

58. The method of claim 42, wherein the ionically conducting membrane is bonded to the gas diffusion cathode.

59. The method of claim 42, further comprising:

operating the electrochemical cell at a current density greater than 1 Ampere per square centimeter.

60. The method of claim 42, further comprising:

operating the electrochemical cell at a current density greater than 0.2 Ampere per square centimeter.

61. An apparatus comprising:

an electrochemical cell having a cation conducting membrane in intimate contact between an anode and a cathodic catalyst layer of a gas diffusion cathode, a source of water in communication with the anode; and a source of oxygen gas and an organic acid vapor in communication with the gas diffusion cathode.

62. The apparatus of claim 61, wherein the gas diffusion cathode comprises a gas diffusion layer having hydrophobic pathways and hydrophilic pathways therethrough.

63. The apparatus of claim 62, wherein the gas diffusion layer is comprised of carbon cloth or carbon paper fiber impregnated with a sintered mass derived from fine carbon powder and a polytetrafluoroethylene emulsion.

64. The apparatus of claim 62, wherein the gas diffusion cathode comprises a gas diffusion layer including carbon cloth or carbon paper fiber impregnated with a carbon-supported pyrolyzed cobalt porphyrin catalyst.

65. The apparatus of claim 61, wherein the cathodic catalyst layer comprises a cation exchange polymer, polytetrafluoroethylene polymer and a metal selected from cobalt, nickel, platinum, palladium, gold, iridium or mixtures thereof.

66. The apparatus of claim 61, wherein the cathodic catalyst layer comprises carbon-supported pyrolyzed cobalt porphyrin.

67. The method of claim 61, wherein the cathodic catalyst layer consists essentially of at least one binder and a form of carbon.

68. The method of claim 67, wherein the at least one binder is selected from polytetrafluoroethylene, a perfluoronated sulfonic acid polymer, and combinations thereof.

69. The method of claim 67, wherein the form of carbon is selected from carbon and graphite.

70. The method of claim 67, wherein the form of carbon has a surface area greater than 200 square meters per gram.

71. The apparatus of claim 61, wherein the cathodic catalyst layer comprises a cation exchange polymer, polytetrafluoroethylene polymer and a carbon-supported pyrolyzed cobalt-porphyrin.

72. The apparatus of claim 61, wherein the anode comprises a substrate selected from porous titanium, titanium suboxides, platinum, tungsten, tantalum, hafnium and niobium.

73. The apparatus of claim 61, wherein the anode comprises an anodic catalyst selected from ruthenium dioxide, platinum-tungsten alloys or mixtures, glassy carbon, platinum, and combinations thereof.

74. The apparatus of claim 61, wherein the cation conducting membrane comprises a perfluoronated sulfonic acid polymer.

75. The apparatus of claim 61, wherein the cathodic catalyst layer is bonded to the cation conducting membrane.

* * * * *

UNITED STATES PATENT AND TRADEMARK OFFICE
CERTIFICATE OF CORRECTION

PATENT NO.     : 6,949,178 B2
DATED          : September 27, 2005
INVENTOR(S)    : Charles L. K. Tennakoon et al.

It is certified that error appears in the above-identified patent and that said Letters Patent is hereby corrected as shown below:

Column 1,
Line 3, insert the following:
-- This invention was made with government support under grant number DMI-0128511 awarded by the National Science Foundation. The government has certain rights in this invention. --.

Signed and Sealed this

Twenty-second Day of November, 2005

JON W. DUDAS
*Director of the United States Patent and Trademark Office*